US011266811B2

(12) United States Patent
Friend et al.

(10) Patent No.: US 11,266,811 B2
(45) Date of Patent: Mar. 8, 2022

(54) HYDRAULICALLY DRIVEN SURGICAL APPARATUS

(71) Applicant: The Regents of the University of California, Oakland, CA (US)

(72) Inventors: James Friend, San Diego, CA (US); Gopesh Tilvawala, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 81 days.

(21) Appl. No.: 16/334,695

(22) PCT Filed: Sep. 20, 2017

(86) PCT No.: PCT/US2017/052561
§ 371 (c)(1),
(2) Date: Mar. 19, 2019

(87) PCT Pub. No.: WO2018/057650
PCT Pub. Date: Mar. 29, 2018

(65) Prior Publication Data
US 2019/0209811 A1    Jul. 11, 2019

Related U.S. Application Data

(60) Provisional application No. 62/397,011, filed on Sep. 20, 2016.

(51) Int. Cl.
*A61M 25/01* (2006.01)
*A61M 25/00* (2006.01)
(Continued)

(52) U.S. Cl.
CPC ....... *A61M 25/0155* (2013.01); *A61B 1/0052* (2013.01); *A61B 1/0057* (2013.01); (Continued)

(58) Field of Classification Search
CPC ........ A61B 17/00234; A61B 2034/301; A61B 2017/00318; A61B 2017/00539; (Continued)

(56) References Cited

U.S. PATENT DOCUMENTS

2005/0004433 A1*  1/2005  Hirata ................. A61B 1/0055
                                              600/152
2006/0084964 A1   4/2006  Knudson et al.
(Continued)

OTHER PUBLICATIONS

Sharma, C. P. et al., "Blood Compatible Materials and Devices: Perspectives Towards the 21st Century." CRC Press, 1990.
(Continued)

*Primary Examiner* — Lauren P Farrar
*Assistant Examiner* — Hamza A Darb
(74) *Attorney, Agent, or Firm* — Mintz Levin Cohn Ferris Glovsky and Popeo, P.C.

(57) ABSTRACT

A hydraulically driven surgical apparatus may be a tube enclosing a first channel filled with a first fluid. Changing a fluid pressure in the first channel may trigger a deformation of the tube. The deformation of the tube may perform an action associated with a surgical procedure. Related methods for steering a hydraulically driven surgical apparatus are also provided.

20 Claims, 11 Drawing Sheets

(51) Int. Cl.
| | |
|---|---|
| A61M 39/02 | (2006.01) |
| A61B 17/00 | (2006.01) |
| A61B 1/00 | (2006.01) |
| A61B 1/005 | (2006.01) |
| A61B 1/015 | (2006.01) |
| A61M 29/00 | (2006.01) |
| A61B 34/30 | (2016.01) |

(52) U.S. Cl.
CPC ...... *A61B 1/00078* (2013.01); *A61B 1/00151* (2013.01); *A61B 1/015* (2013.01); *A61B 17/00234* (2013.01); *A61M 25/00* (2013.01); *A61M 25/0032* (2013.01); *A61M 29/00* (2013.01); *A61M 39/02* (2013.01); *A61B 2017/00318* (2013.01); *A61B 2017/00539* (2013.01); *A61B 2034/301* (2016.02); *A61M 2039/0205* (2013.01); *A61M 2039/0279* (2013.01)

(58) Field of Classification Search
CPC ... A61B 1/00151; A61B 1/015; A61B 1/0057; A61B 1/00078; A61B 1/0052; A61M 2039/0205; A61M 2039/0279; A61M 25/0133; A61M 25/0155
See application file for complete search history.

(56) References Cited

U.S. PATENT DOCUMENTS

| | | | | |
|---|---|---|---|---|
| 2007/0100235 | A1* | 5/2007 | Kennedy, II | A61M 25/0136 600/434 |
| 2010/0010437 | A1 | 1/2010 | Miles et al. | |
| 2010/0256558 | A1* | 10/2010 | Olson | A61B 34/20 604/95.01 |

OTHER PUBLICATIONS

Bergeles, Christos et al., "From passive tool holders to microsurgeons: safer, smaller, smarter surgical robots." Biomedical Engineering, IEEE Transactions on, 61(5):1565-1576, 2014.
Bonita, Ruth et al., "Subarachnoid hemorrhage: epidemiology, diagnosis, management, and outcome." Stroke, 16(4):591-594, 1985.
Brain aneurysm statistics. http://www.bafound.org/Statistics_and_Facts.
Broadbent, L. Paul et al., "Transfer of a self-expanding stent to a braided microcatheter with the aid of transcatheter illumination: Technical report and illustrative case." American Journal of Neuroradiology, 24(8):1517-1519, 2003.
Brown, Robert D. et al., "Unruptured intracranial aneurysms: epidemiology, natural history, management options, and familial screening." The Lancet Neurology, 13(4):393-404, 2014.
Daerden, Frank et al., "Pneumatic artificial muscles: actuators for robotics and automation." European Journal of Mechanical and Environmental Engineering, 47(1):11-21, 2002.
Dargahi, J. et al., "Human tactile perception as a standard for artificial tactile sensing—a review." The International Journal of Medical Robotics and Computer Assisted Surgery 1, 23-35 (2004).
Darsaut, Tim E. et al., "Fatal avulsion of choroidal or perforating arteries by guidewires case reports, ex vivo experiments, potential mechanisms and prevention." Interventional Neuroradiology, 20(3):251-260, 2014.
De Voider, Michael et al., "Pneumatic and hydraulic microactuators: a review." Journal of Micromechanics and microengineering, 20(4):043001, 2010.
Doerfler, Arnd et al., "Aneurysmal rupture during embolization with guglielmi detachable coils: causes, management, and outcome." American Journal of Neuroradiology, 22(10):1825-1832, 2001.
Friend, J. et al., "Fabrication of microfluidics devices using polydimethylsiloxane (pdms)." Biomicrofluidics 4, 026502 (2009).

Friend, J. R. et al., "Microscale acoustofluidics: Microfluidics driven via acoustics and ultrasonics." Reviews of Modern Physics 83, 647-704 (2011).
Fukuda, Hitoshi et al., "Endovascular therapy for ruptured cerebral aneurysms in the elderly: Poor accessibility of the guiding catheter and use of local anesthesia as the predictors of procedure-related rupture." Neurosurgery, 77(4):544-552, 2015.
Fusco, Stefano et al., "An integrated microrobotic platform for on-demand, targeted therapeutic interventions." Advanced Materials, 26(6):952-957, 2014.
Gent, A.N., "Elastic instabilities in rubber." International Journal of Non-Linear Mechanics, 40(2):165-175, 2005.
Glass, N. R. et al., "Organosilane deposition for microfluidic applications." Biomicrofluidics 5, 036501 (2011). URL http://dx.doi.org/doi/10.1063/1.3625605.
Guglielmi, G. et al., "Electrothrombosis of saccular aneurysms via endovascular approach: part 2: preliminary clinical experience." Journal of Neurosurgery, 75(1):8-14, 1991.
Guglielmi, G. et al., "Endovascular treatment of posterior circulation aneurysms by electrothrombosis using electrically detachable coils." Journal of Neurosurgery 77, 515-524 (1992).
Guglielmi, G. "History of endovascular endosaccular occlusion of brain aneurysms: 1965-1990." Interventional Neuroradiology 13, 217-224 (2007).
Hetts, S. W. et al., "Magnetically-assisted remote controlled microcatheter tip deflection under magnetic resonance imaging." Journal of visualized experiments: JoVE (2013).
Hop, J. W. et al., "Case-fatality rates and functional outcome after subarachnoid hemorrhage a systematic review." Stroke 28, 660-664 (1997).
Ilievski, Filip et al., "Soft robotics for chemists." Angewandte Chemie, 123(8):1930-1935, 2011.
Jeong, Ok Chan et al., "All PDMS Pneumatic Microfinger with Bidirectional Motion and its Application." Microelectromechanical Systems, Journal of, 15(4):896-903, 2006.
Jeong, Ok Chan et al., "Pneumatic micro finger as endeffecter of robot." In Micro-NanoMechatronics and Human Science, 2005 IEEE International Symposium on, pp. 145-148. IEEE, 2005.
Juvela, S. et al., "Natural history of unruptured intracranial aneurysms: a long-term follow-up study." Journal of neurosurgery 79, 174-182 (1993).
Kim, Dae-Hyeong et al., "Materials for multifunctional balloon catheters with capabilities in cardiac electrophysiological mapping and ablation therapy." Nature Materials, 10(4):316-323, 2011.
Konishi, S. et al., "Thin flexible end-effector using pneumatic balloon actuator." Sensors and Actuators A: Physical, 89(1):28-35, 2001.
Levy, Elad et al., "Rupture of intracranial aneurysms during endovascular coiling: management and out-comes." Neurosurgery, 49(4):807-813, 2001.
Lu, Yen-Wen et al., "Microhand for biological applications." Applied Physics Letters, 89(16):164101, 2006.
Makowski, H. "The properties of Fluosol-DA infusion in the treatment of hemorrhagic shock." In Proceedings on the IV International Symposium on Perfluorochemical Blood Substitutes, Kyoto, pp. 439-448, 1978.
Manor, O. et al., "Substrate dependent drop deformation and wetting under high frequency vibration." Soft Matter 7, 7976-7979 (2011).
Martinez, Ramses V. et al., "Robotic tentacles with three-dimensional mobility based on flexible elastomers." Advanced Materials, 25(2):205-212, 2013.
Molyneux, A. et al., "Risk of Recurrent Subarachnoid Haemorrhage, Death, or Dependence and Standardised Mortality Ratios After Clipping or Coiling of an Intracranial Aneurysm in the International Subarachnoid Aneurysm Trial (ISAT): Long-Term Follow-Up." The Lancet Neurology 8, 427-433 (2009).
Mooney, M., "A theory of large elastic deformation." Journal of Applied Physics, 11(9):582-592, 1940.
Murayama, Y. et al., "Embolization of incidental cerebral aneurysms by using the Guglielmi detachable coil system." J. Neurosurg 90, 207-214 (1999).

(56) References Cited

OTHER PUBLICATIONS

Murayama, Y. et al., "Risk analysis of unruptured intracranial aneurysms prospective 10-year cohort study." Stroke 115 (2016).
Okayasu, Haruna et al., "Development of a hydraulic-driven flexible manipulator for neurosurgery." In International Congress Series, vol. 1256, pp. 607-612. Elsevier, 2003.
Paek, Jungwook et al., "Microrobotic tentacles with spiral bending capability based on shape-engineered elastomeric microtubes." Scientific Reports, 5, 2015.
Pang, Changlin et al., "Electrolysis-based parylene balloon actuators for movable neural probes." In Nano/Micro Engineered and Molecular Systems, 2007. NEMS'07. 2nd IEEE International Conference on, pp. 913-916. IEEE, 2007.
Parry, D.A. et al., "The hydraulic mechanism of the spider leg." Journal of Experimental Biology, 36(2):423-433, 1959.
Qureshi, Adnan I. et al., "Comparison of endovascular and surgical treatments for intracranial aneurysms: an evidence-based review." The Lancet Neurology, 6(9):816-825, 2007.
Raftopoulos, Christian et al., "Prospective analysis of aneurysm treatment in a series of 103 consecutive patients when endovascular embolization is considered the first option." Journal of Neurosurgery, 93(2): 175-182, 2000.
Regli, Luca wt al., "Endovascular coil placement compared with surgical clipping for the treatment of unruptured middle cerebral artery aneurysms: a consecutive series." Journal of Neurosurgery, 90(6): 1025-1030, 1999.
Rinkel, Gabriel J.E. et al., "Prevalence and risk of rupture of intracranial aneurysms a systematic review." Stroke, 29(1):251-256, 1998.
Rinne, Jaakko et al., "Multiple intracranial aneurysms in a defined population: prospective angiographic and clinical study." Neurosurgery, 35(5):803-808, 1994.
Rivlin, R.S. "Large elastic deformations of isotropic materials, iv. further developments of the general theory." Philosophical Transactions of the Royal Society of London A: Mathematical, Physical and Engineering Sciences, 241(835):379-397, 1948.
Ruzzu, A. et al., "Positioning system for catheter tips based on an active microvalve system." Journal of Micromechanics and Microengineering, 8(2):161, 1998.
Schwoerer, M et al., "Fluidic microjoints based on spider legs." In Conf. on New Actuators (Bremen), 1998.
Shepherd, Robert F. et al., "Multigait soft robot." Proceedings of the National Academy of Sciences, 108(51):20400-20403, 2011.
Simaan, Nabil et al., "A dexterous system for laryngeal surgery." In Robotics and Automation, 2004. Proceedings. ICRA'04. 2004 IEEE International Conference on, vol. 1, pp. 351-357. IEEE, 2004.
Sluzewski, Menno et al., "Rupture of intracranial aneurysms during treat-ment with guglielmi detachable coils: incidence, outcome, and risk factors." Journal of Neurosurgery, 94(2):238-240, 2001.
Stone, D. H. et al., "The financial implications of endovascular aneurysm repair in the cost containment era." Journal of Vascular surgery 59, 283-290 (2014).

Suzumori, Koichi et al., "Applying a flexible microactuator to robotic mechanisms." Control Systems, IEEE, 12(1):21-27, 1992.
Suzumori, Koichi et al., "Flexible microactuator for miniature robots." In Micro Electro Mechanical Systems, 1991, MEMS'91, Proceedings. An Investigation of Micro Structures, Sensors, Actuators, Machines and Robots. IEEE, pp. 204-209. IEEE, 1991.
Suzumori, Koichi et al., "Integrated flexible microactuator systems." Robotica, 14(05):493-498, 1996.
Suzumori, Koichi et al., "Microfabrication of integrated FMAS using stereo lithography." In Micro Electro Mechanical Systems, 1994, MEMS'94, Proceedings, IEEE Workshop on, pp. 136-141. IEEE, 1994.
Taussky, Ph et al., "A checklist in the event of aneurysm perforation during coiling." American Journal of Neuroradiology, 31(7):E59-E59, 2010.
Tolley, Michael T. et al., "A resilient, untethered soft robot." Soft Robotics, 1(3):213-223, 2014.
Trivedi, Deepak et al., "Soft robotics: Biological inspiration, state of the art, and future research." Applied Bionics and Biomechanics, 5(3):99-117, 2008.
Vitiello, Valentina et al., "Emerging robotic platforms for minimally invasive surgery." Biomedical Engineering, IEEE Reviews in, 6:111-126, 2013.
Wakhloo, A. et al., "Revolution in Aneurysm Treatment: Flow Diversion to Cure Aneurysms: A Paradigm Shift." J. Neurosurg. 61,111-120 (2014).
Watanabe, Yoshihiro et al., "Small, soft, and safe microactuator for retinal pigment epithelium transplantation." In Micro Electro Mechanical Systems, 2007. MEMS. IEEE 20th International Conference on, pp. 659-662. IEEE, 2007.
Wehner, Michael et al., "An integrated design and fabrication strategy for entirely soft, autonomous robots." Nature, 536(7617):451-455, 2016.
Wei, Wei et al., "A compact two-armed slave manipulator for minimally invasive surgery of the throat." In The First IEEE/RAS-EMBS International Conference on Biomedical Robotics and Biomechatronics, 2006. BioRob 2006., pp. 769-774. IEEE, 2006.
Wiebers, David O. et al., "Impact of unruptured intracranial aneurysms on public health in the united states." Stroke, 23(10): 1416-1419, 1992.
Wiebers, D. O. "Unruptured intracranial aneurysms: natural history, clinical outcome, and risks of surgical and endovascular treatment." The Lancet 362, 103-110 (2003).
Wiggins, G. P. et al., "Understanding by Design" (ASCD, 2005).
Yoshida, K. et al., "A microgripper using electro-rheological fluid." In ICCAS-SICE, 2009, pp. 2987-2990. IEEE, 2009.
Yun, Cheol-Ho et al., "Multi-degree-of-freedom ultrasonic micromotor for guidewire and catheter navigation: The neuroglide actuator." Applied Physics Letters, 100(16):164101, 2012.
Zhang, Yi J. et al., "Brain aneurysms." In Emergency Approaches to Neurosurgical Conditions, p. 89-101. Springer, 2015.
Singer, Robert J. et al., "Etiology, clinical manifestations, and diagnosis of aneurysmal subarachnoid hemorrhage." UpToDate. Waltham, MA, 2012.

\* cited by examiner

HYDRAULICALLY DRIVEN SURGICAL APPARATUS

RELATED APPLICATION

This application is a national phase entry of Patent Cooperation Treaty Application PCT/US2017/052561 filed Sep. 20, 2017, entitled "HYDRAULICALLY DRIVEN SURGICAL APPARATUS," which claims the benefit of U.S. Provisional Application 62/397,011 filed on Sep. 20, 2016, entitled "NEUROSURGICAL OUTCOMES WITH HYDRAULIC DRIVEN, MINIMALLY-INVASIVE MICRO ACTUATORS," the disclosures of which are incorporated herein by reference in their entirety.

TECHNICAL FIELD

The subject matter disclosed herein relates generally to endovascular neurosurgery and more specifically to a hydraulically steered surgical apparatus for use during endovascular neurosurgery.

BACKGROUND

Endovascular neurosurgery may be conducted to prevent, diagnose, and/or treat a variety of neurological disorders including, for example, cerebral aneurysms, arteriovenous malformation, arteriovenous fistulas, carotid stenosis, strokes, spinal malformations, vasospasms, and/or the like. For example, endovascular embolization is a type of endovascular neurosurgery for treating cerebral aneurysms. During the procedure, a catheter may be moved through a patient's blood vessel to the site of the aneurysm in the patient's brain. Upon reaching the aneurysm, the catheter may be used to deposit one or more substances for sealing the aneurysm including, for example, metal coils, plastic particles, glue, foam, balloons, and/or the like. The same and/or similar procedure may also be used to treat other disorders including, for example, arteriovenous malformation, arteriovenous fistulas, and/or the like.

SUMMARY

Articles of manufacture, including a hydraulically driven surgical apparatus, and methods for steering the hydraulically driven surgical apparatus are provided. A hydraulically driven surgical apparatus may include a tube enclosing a first channel filled with a first fluid. A first change in a fluid pressure in the first channel may trigger a first deformation of the tube. The first deformation of the tube may perform an action associated with a surgical procedure In some variations, one or more features disclosed herein including the following features can optionally be included in any feasible combination. The first channel may be a channel traversing laterally through at least a portion of an interior of the tube. At least a portion of the tube may bend in response to the change in the fluid pressure. The first channel may form a helix. At least a portion of the tube may twist in response to the change in the fluid pressure In some variations, the tube may further enclose a second channel. The second channel may be filled with a second fluid. A second change in a pressure of the second fluid in the second channel may trigger the first deformation and/or a second deformation of the tube. The second deformation may occur in a different portion of the tube, have a different orientation, and/or have a different degree as the first deformation. The second channel may provide a passageway for a substance, a device, and/or a tool. The first channel may have a different shape and/or dimension as the second channel. The first channel may traverse a different portion of the tube as the second channel.

In some variations, the first fluid may include a contrast agent for increasing a visibility of the tube to enable medical imaging. The action may include aligning the tube with a treatment location of the surgical procedure. The action may include advancing and/or retracting the tube. The tube may be coupled with a tool and the first deformation of the tube may move the tool to perform the action. The tool may be a gripper, a drill, a cauterizer, and/or a cutter.

In some variations, the apparatus may be coupled with a controller configured to at least: receive, from a user, one or more inputs; and change, based at least on the one or more inputs, the fluid pressure in the first channel. The controller may include at least one fluid chamber coupled with the first channel. The controller may change the fluid pressure in the first channel by at least adjusting a compression against the at least one fluid chamber. The one or more inputs may include a mechanical input, a digital input, and/or a haptic input.

In some variations, the tube may be formed from a soft and/or deformable material. The soft and/or deformable material may include a contrast agent for enhancing a visibility of the tube to enable medical imaging.

A method for steering a hydraulically driven surgical apparatus may include changing a fluid pressure in a channel filled with a fluid. The channel may be enclosed by a tube comprising the hydraulically driven surgical apparatus. The change in the fluid pressure may trigger a deformation of the tube. The deformation of the tube may perform an action associated with a surgical procedure.

In some variations, the fluid pressure in the channel may be changed by at least adjusting a compression against a fluid chamber coupled with the channel. The action may include aligning the tube with a treatment location of the surgical procedure. The deformation of the tube may perform the action by at least actuating a tool coupled with the tube.

In some variations, one or more inputs may be received from a user. The fluid pressure in the channel may be changed based at least on the one or more inputs. The one or more inputs may include a mechanical input, a digital input, and/or a haptic input.

A hydraulically driven surgical apparatus may include means for changing a fluid pressure in a channel filled with a fluid. The channel may be enclosed by a tube comprising the apparatus. The change in the fluid pressure may trigger a deformation of the tube. The deformation of the tube may perform an action associated with a surgical procedure.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to endovascular neurosurgery, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the subject matter disclosed herein. In the drawings.

When practical, similar reference numbers denote similar structures, features, or elements.

DETAILED DESCRIPTION

A guidewire is typically used for moving a catheter through a blood vessel to a treatment location such as, for example, the site of aneurysm and/or the like. Because the aneurysm extrudes from the side of the blood vessel, the guidewire may include a flanged tip for aligning the catheter within the dome of the aneurysm. However, a conventional guidewire cannot be steered through the complex geometry of a blood vessel. In particular, the flanged tip has a fixed curvature that cannot be changed in vivo. Thus, a conventional guidewire is likely to rupture the walls of the blood vessel while being maneuvered through the blood vessel.

In some example embodiments, a hydraulically driven surgical apparatus may be used for moving a catheter through a blood vessel. Instead of a flanged tip having a fixed curvature, the hydraulically driven surgical apparatus may be formed from a soft tube, which may be deformed in vivo in order to steer the surgical apparatus into alignment with a treatment location. For example, the tip and/or other portions of the tube may be bent, via hydraulic forces, to align within the dome of an aneurysm. The absence of a flanged tip and the soft construction of the hydraulically driven surgical apparatus may eliminate the risk of puncturing a blood vessel, thereby increasing the maneuverability of the hydraulically driven surgical apparatus.

Figure 1A:
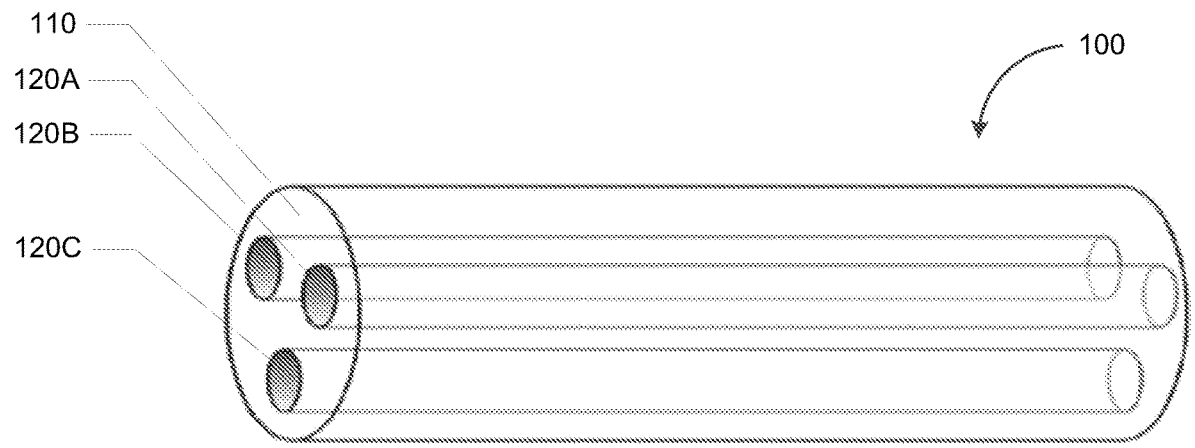
FIG. 1A depicts a perspective view of a cross section of a hydraulically driven surgical apparatus, in accordance with some example embodiments.

FIG. 1A depicts a perspective view of a cross section of a hydraulically driven surgical apparatus 100, in accordance with some example embodiments. Referring to FIG. 1A, the surgical apparatus 100 may include a tube 110. The tube 110 may enclose one or more channels, which may traverse laterally through at least a portion of an interior of the tube 110. For example, as shown in FIG. 1A, the tube 110 may enclose a first channel 120A, a second channel 120B, and a third channel 120C. Although the tube 110 is shown to enclose three channels, it should be appreciated that the tube 110 may enclose other quantities of channels. Furthermore, the first channel 120A, the second channel 120B, and the third channel 120C may be have any orientation relative to one another including and/or in addition to, for example, the parallel configuration shown in FIG. 1A.

In some example embodiments, the tube 110 including the first channel 120A, the second channel 120B, and/or the third channel 120C may be formed from a pliable material such as, for example, silicone rubber. The material may include one or more contrast agents such as, for example, tantalum and/or the like, for enhancing the visibility of the tube 110 for medical imaging such as, for example, X-rays and/or the like. It should be appreciated that medical imaging may be performed during a surgical procedure such as, for example, endovascular embolization and/or the like, in order to track the position and/or progress of the surgical apparatus within a patient's blood vessel.

Referring to FIG. 1A, the first channel 120A, the second channel 120B, and/or the third channel 120C may be filled with a fluid. It should be appreciated that the first channel 120A, the second channel 120B, and/or the third channel 120C may be filled with a fluid instead of a gas in order to minimize the risk for introducing air bubbles into a blood vessel and causing a potentially fatal air embolism. Alternatively and/or additionally, the first channel 120A, the second channel 120B, and/or the third channel 120C may be a lumen that is left as a cavity in order to serve as a passageway for a substance and/or other apparatuses (e.g., guidewires, catheters, hollow tubes, fluid-filled tubes, and/or the like).

In some example embodiments, the first channel 120A, the second channel 120B, and/or the third channel 120C may be filled with biocompatible and/or hemocompatible fluid such as, for example, saline and/or the like. Alternatively and/or additionally, the fluid may include one of more contrast agents such as, for example, iodine (I), barium (Ba), and/or the like. It should be appreciated that contrast agents may enhance the contrast of the tube 110 for medical imaging such as, for example, X-rays and/or the like. As such, the inclusion of the contrast agent in the fluid may increase the visibility of the tube 110 within the body, for example, as the tube 110 is being moved through a blood vessel.

According to some example embodiments, the first channel 120A, the second channel 120B, and/or the third channel 120C may be configured to respond to changes in fluid pressure by undergoing an axial deformation but not a radial deformation. As used herein, axial deformation may refer to a change in length while radial deformation may refer to a change in diameter. As such, changes in fluid pressure may cause a change in the length of the first channel 120A, the second channel 120B, and/or the third channel 120C. However, changes in fluid pressure may cause a minimal change in the respective diameters of the first channel 120A, the second channel 120B, and/or the third channel 120C. For example, changing the fluid pressure in the first channel 120A, the second channel 120B, and/or the third channel 120C may cause the first channel 120A, the second channel 120B, and/or the third channel 120C to distend and/or contract lengthwise. Meanwhile, the diameter of the first channel 120A, the second channel 120B, and/or the third channel 120C may remain constant notwithstanding the changes in fluid pressure within the first channel 120A, the second channel 120B, and/or the third channel 120C.

Figure 1B:
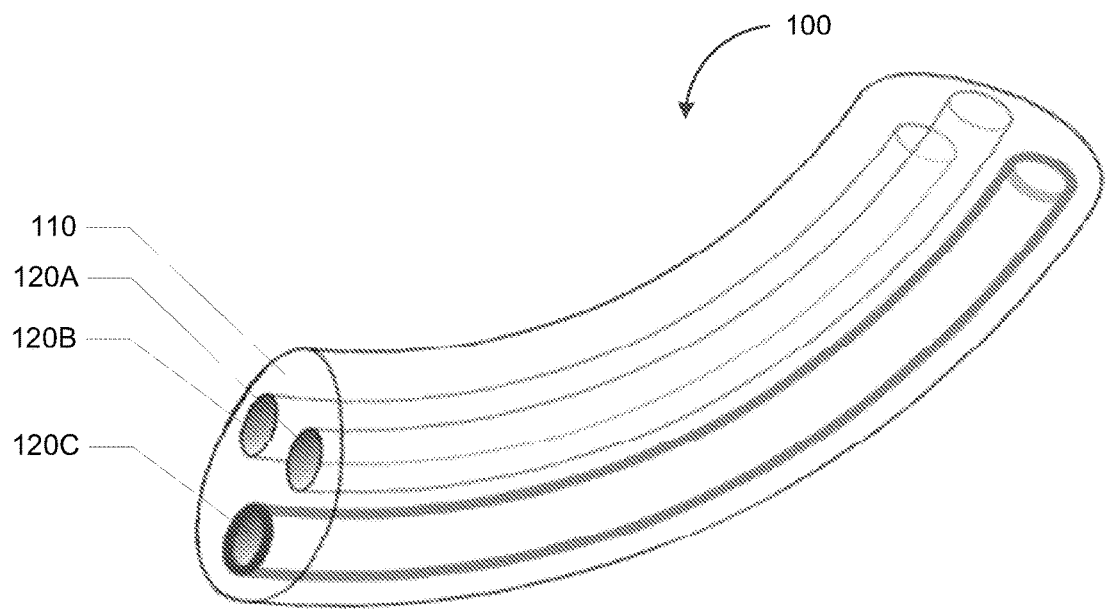
FIG. 1B depicts a deformation of a hydraulically driven surgical apparatus, in accordance with some example embodiments.

The changes in the length of the first channel 120A, the second channel 120B, and/or the third channel 120C may cause a deformation of the tube 110. For example, changing the fluid pressure in the first channel 120A, the second channel 120B, and/or the third channel 120C may trigger the formation of a bend in one or more portions of the tube 110. To further illustrate, FIG. 1B depicts a deformation of the hydraulically driven surgical apparatus 100, in accordance with some example embodiments. Changing the fluid pressure in different channels and/or different combination of channels may cause a deformation of the tube 110 that differs in type, extent, orientation, and/or the like. For instance, as shown in FIG. 1B, increasing the fluid pressure in the third channel 120C may lengthen the third channel 120C and cause the tube 110 to bend in one direction. Although not shown, it should be appreciated that increasing the fluid pressure in the first channel 110A and/or the second channel 110B may cause the tube 110 to bend in other directions.

It should be appreciated that the aspect ratio of a channel may be configured to both maximize the channel's tendency to distend lengthwise and minimize the channel's tendency to expand in width (or diameter). The relationship between the dimension D of a channel, the strain σ against the channel due to fluid pressure, and the resulting deformation ΔD of the channel is shown by Equation (1) below. It should be appreciated that the dimension D may be the length of the channel or the width of the channel. Meanwhile, ΔD may refer to either a corresponding change in the length of the channel or a change in the width of the channel. As Equation (1) indicates, where the length of the channel is magnitudes larger than the width of the channel, the same quantity of strain σ may trigger a much larger change in the length of the channel than in the width of the channel.

$$\Delta D = D \times \sigma \quad (1)$$

In some example embodiments, the millimeter scale length of the first channel 120A, the second channel 120B, and/or the third channel 120C may be orders of magnitudes larger than the micrometer scale width of the channels. As such, based on Equation (1), changes in fluid pressure may trigger a change in the length but not in the width of the first channel 120A, the second channel 120B, and/or the third channel 120C.

Alternatively and/or additionally, the channel may be formed from a material that prevents an excessive change in the length and/or the width of the channel. For example, in some example embodiments, the first channel 120A, the second channel 120B, and/or the third channel 120C may be formed from a material exhibiting nonlinear elasticity such as, for example, a polymer. To further illustrate nonlinear elasticity, FIG. 1G depicts a graph 160 illustrating stress-strain curves for different materials, in accordance with some example embodiments.

Figure 1C:
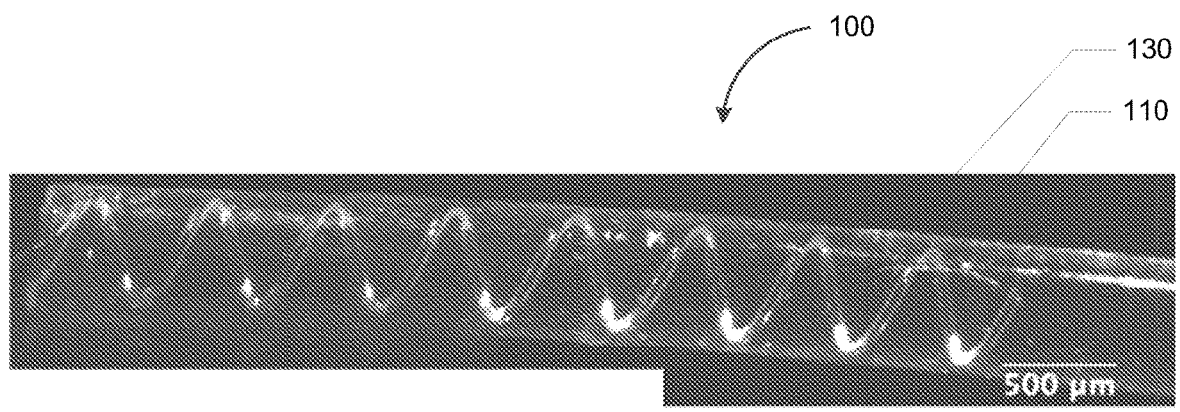
FIG. 1C depicts another configuration for a hydraulically driven surgical apparatus, in accordance with some example embodiments.
Figure 1D:
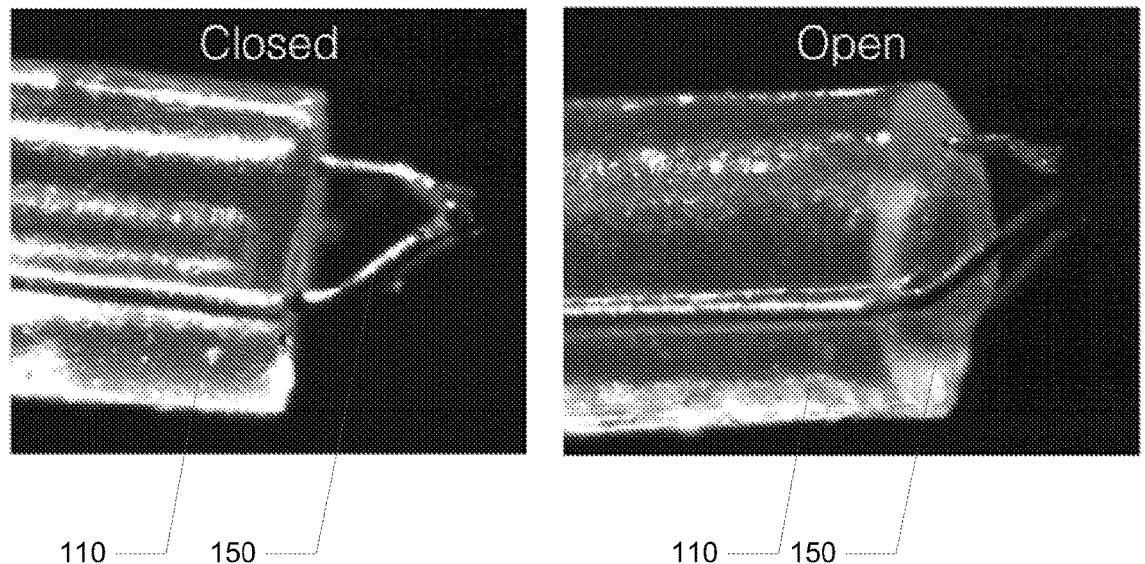
FIG. 1D depicts another configuration for a hydraulically driven surgical apparatus, in accordance with some example embodiments.
Figure 1E:
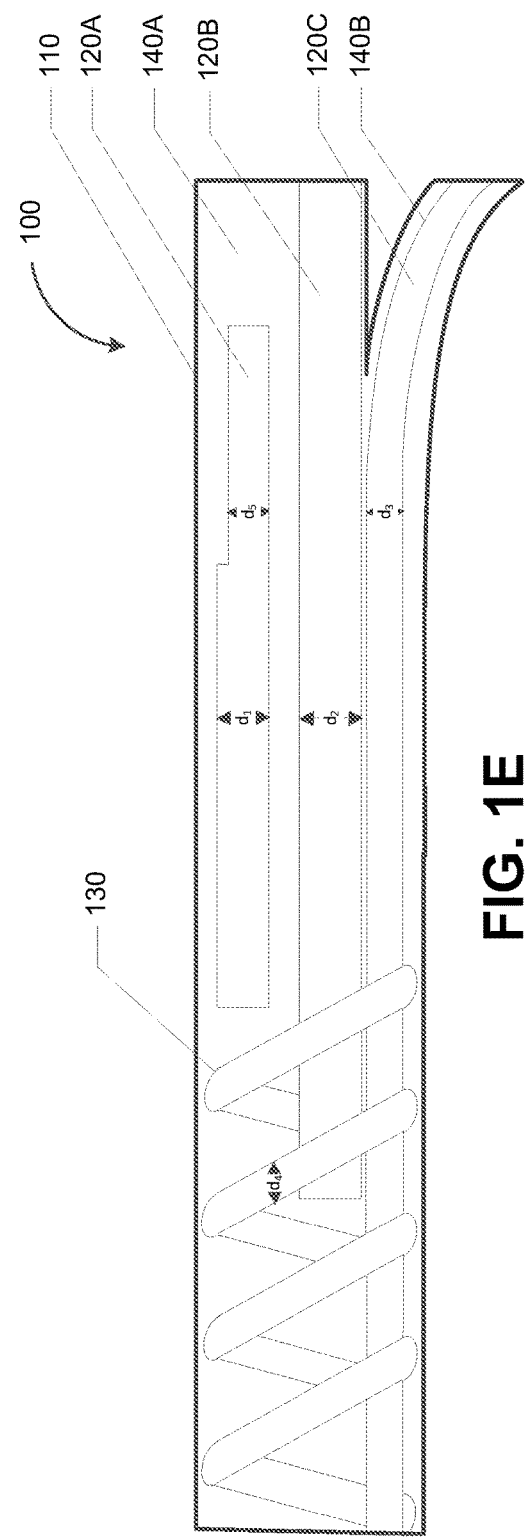
FIG. 1E depicts another configuration for a hydraulically driven surgical apparatus, in accordance with some example embodiments.
Figure 1F:
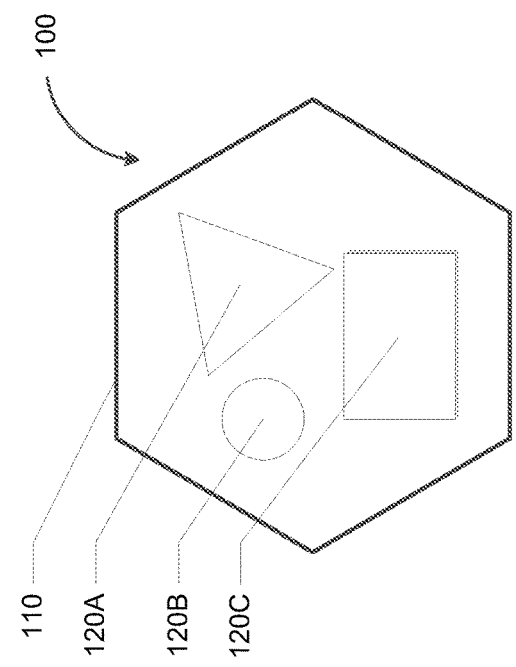
FIG. 1F depicts another configuration for a hydraulically driven surgical apparatus, in accordance with some example embodiments.
Figure 1G:
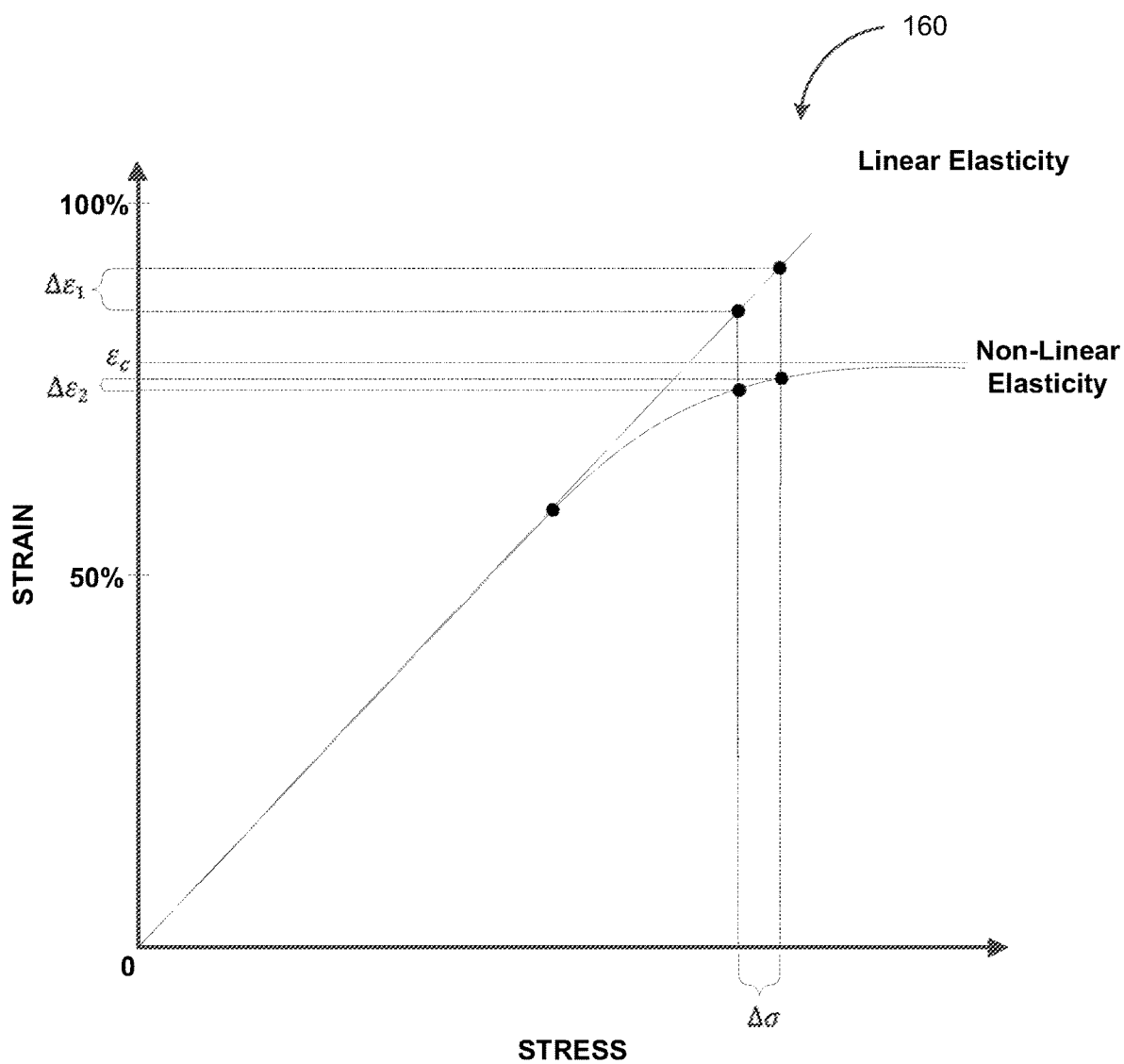
FIG. 1G depicts a graph illustrating stress-strain curves for different materials, in accordance with some example embodiments.

Referring to FIG. 1G, the pressure applied against the interior of a channel may be quantified as stress while the channel's response to the pressure, including by expanding in length and/or width, may be quantified as strain. A change in stress (e.g., Δσ) may trigger a corresponding change in strain (e.g., Δε). The magnitude of the change in strain may depend on whether the channel is formed from a linear elastic material or a non-linear elastic material.

As shown in FIG. 1G, some materials may exhibit linear elasticity, in which case the stress-strain curve for that material may a straight line on the graph 160. A channel formed from a material having linear elasticity may show a constant increase in strain when subject to a given increment in stress. For instance, the channel may respond to an increment in stress Δσ by showing an increment in strain $\Delta\varepsilon_1$. Such a channel may continue to expand in length and/or width when subject to growing quantities of stress. By contrast, a channel formed from a material having non-linear elasticity may show a lesser increase in strain when subject to the same increment in stress. For example, the channel may respond to the same increment in stress Δσ by showing a smaller increment in strain $\Delta\varepsilon_2$.

Moreover, a channel formed from a material having non-linear elasticity may have a critical strain $\varepsilon_c$, which may be a maximum amount of strain after which point the channel may cease to expand in length and/or in width even as the channel is subject to growing stress. Where the length of the channel is magnitudes larger than the width of the channel, the channel may have a significantly lower critical strain for widthwise expansion than for lengthwise expansion. As such, the channel may continue to distend lengthwise even though the channel has ceased to expand in width. This limit to the channel's tendency to expand, particularly in width, may prevent a hazardous overexpansion of the tube 110 while the tube 110 is disposed within a blood vessel, for example, during a surgical procedure (e.g., endovascular procedure).

In some example embodiments, the deformation of the tube 110 may perform an action associated with a surgical procedure such as, for example, endovascular embolization and/or the like. The action associated with the surgical procedure may include steering the tube 110 into alignment with a treatment location including by, for example, bending the tip and/or other portions of the tube 110 towards the dome of an aneurysm. Alternatively and/or additionally, the action may include advancing and/or retracting at least a portion the tube 110, and/or actuating a surgical tool (e.g., gripper, cutter, drill, cauterizer, and/or the like) coupled with the surgical apparatus.

The responsiveness of the tube 110 to changes in fluid pressure including, for example, the degree, the type, and/or orientation of the deformation exhibited by the tube 110 in response to changes in fluid pressure, may be determined based a number of factors including, for example, the dimensions of the tube 110, the dimensions of the channels, the shape of the tube 110, the shape of the channels, the viscosity of the fluid filling the channels, the material forming the tube 110 and/or the channels, and/or the like.

To further illustrate, Equations (2) and (3) below illustrate the relationship between the pressure P applied to a channel (e.g., the third channel 120C) and the deformation of the tube 110 as quantified, for example, by an angle of deflection θ of the tube 110.

$$\theta = \int_0^1 \frac{d^2 y}{dx^2} ds \qquad (2)$$

$$\frac{d^2 y}{dx^2} = \frac{P\pi r^2 d}{E' I} \left[ 1 + \left( \frac{dx}{dy} \right)^2 \right]^{3/2} \qquad (3)$$

wherein y=y(x) may be the finite lateral movement of the tube 110, P may be the pressure applied to the third channel 120C, r may be a radius of the third channel 120C, E' may be a bulk modulus taken from a generalized Mooney-Rivlin model for a material forming the third channel 120C, I may be a moment of inertia of the tube 110, and d may be a width or a diameter of the tube 110.

FIG. 1C depicts another configuration for the hydraulically driven surgical apparatus 100, in accordance with some example embodiments. Referring to FIG. 1C, the tube 110 may enclose one or more helix (e.g., spiral in form) channels instead of and/or in addition to the channels shown in FIGS. 1A-B. For example, as shown in FIG. 1C, the tube 110 may enclose a fourth channel 130, which may be a helix channel that traverses laterally through the interior of the tube 110. The fourth channel 130 may be filled with a fluid. Furthermore, the fourth channel 130 may also respond to changes in fluid pressure by changing in length but not in width. In some example embodiments, the change in fluid pressure in the fourth channel 130 may cause the tube 100 to twist in a spiraling pattern. The twisting of the tube 110 may further cause at least a portion of the tube 110 to advance and/or retract during, for example, a surgical procedure.

FIG. 1D depicts another configuration for the hydraulically driven surgical apparatus 100, in accordance with some example embodiments. In some example embodiments, the tube 110 may be coupled with one or more surgical tools or tools such as, for example, a gripper, a cutter, a drill, a cauterizer, and/or the like.

The motion and/or the deformation of the tube 110 may actuate and/or maneuver the surgical tool. For instance, as shown in FIG. 1D, the tip of the tube 110 may include a gripper. As noted, changes in fluid pressure in the first channel 120A, the second channel 120B, the third channel 120C, and/or the fourth channel 130, may cause a deformation in one or more portions of the tube 110. This deformation may further actuate the surgical tools coupled with the tube 110. For instance, deforming one or more portions of the tube 110 may cause the jaws of the gripper to open and/or to close. In some example embodiments, the jaws of the gripper may be opened and/or closed to perform a variety of actions including, for example, suturing and/or the like.

FIG. 1E depicts another configuration for the hydraulically driven surgical apparatus 100, in accordance with some example embodiments. Referring to FIG. 1E, the tube 110 may enclose both straight channels and/or helix channels including, for example, the first channel 120A, the second channel 120B, the third channel 120C, and/or the fourth channel 130. It should be appreciated that the first channel 120A, the second channel 120B, the third channel 120C, and/or the fourth channel 130 may have the same and/or different dimensions including, for example, channel length, channel diameter, channel height, channel width, and/or the like.

To further illustrate, FIG. 1E shows the first channel 120A, the second channel 120B, the third channel 120C, and/or the fourth channel 130 as having different lengths. For example, the third channel 120C may have a same length as the tube 110 and may therefore extend the entire length of the tube 110 from one end of the tube 110 to the other end of the tube 110. By contrast, the first channel 120A, the second channel 120B, the third channel 120C, and/or the fourth channel 130 may have varying lengths and may therefore start and/or terminate at different points along the length of the tube 110.

Alternatively and/or additionally, the first channel 120A, the second channel 120B, the third channel 120C, and/or the fourth channel 130 may have different diameters. For example, the first channel 120A may have a first diameter $d_1$, which may be wider and/or more narrow than a second diameter $d_2$ of the second channel 120B, a third diameter $d_3$ of the third channel 120C, and/or a fourth diameter $d_4$ of the fourth channel 140.

Furthermore, the dimensions of a channel may change. For instance, the diameter, height, and/or width of a channel may taper and/or expand at one or more points along the length of the channel. To further illustrate, FIG. 1E shows that a first portion of the first channel 120A may have the first diameter $d_1$ while a second portion of the first channel 120A may have a fifth diameter $d_5$ that is different than the first diameter $d_1$.

Referring again to FIG. 1E, it should be appreciated that the tube 110 may split into multiple branches including, for example, a first branch 140A and a second branch 140B. Some channels may extend through one branch of the tube 110 while other channels may extend through a different branch of the tube 110. For example, as shown in FIG. 1E, the first channel 120A and the second channel 120B may extend through the first branch 140A of the tube 110 whereas the third channel 120C may extend through the second branch 140B of the tube 110.

FIG. 1F depicts another configuration for the hydraulically driven surgical apparatus 100, in accordance with some example embodiments. In some example embodiments, the tube 110 as well as the channels enclosed by the tube 110 may have any shape. For instance, the tube 110 and/or the enclosed channels may be circular. Alternatively and/or additionally, the tube 110 and/or the enclosed channels may be any type of polygon including, for example, equilateral polygons, regular polygons, non-equilateral polygons, non-regular polygons, and/or the like.

To further illustrate, FIG. 1F shows a cross section of the surgical apparatus 100. As shown in FIG. 1F, the tube 110 may be hexagonal and/or a different shape. Meanwhile, the first channel 120A may be triangular and/or a different shape, the second channel 120B may be circular and/or a different shape, and the third channel 120C may be rectangular and/or a different shape. It should be appreciated that shape of the tube 110 and/or any channel enclosed therein may change at various points along their respective lengths. For example, a first portion of the tube 110 may be one shape (e.g., hexagonal) while a second portion of the tube 110 may be a different shape (e.g., circular).

Figure 2:
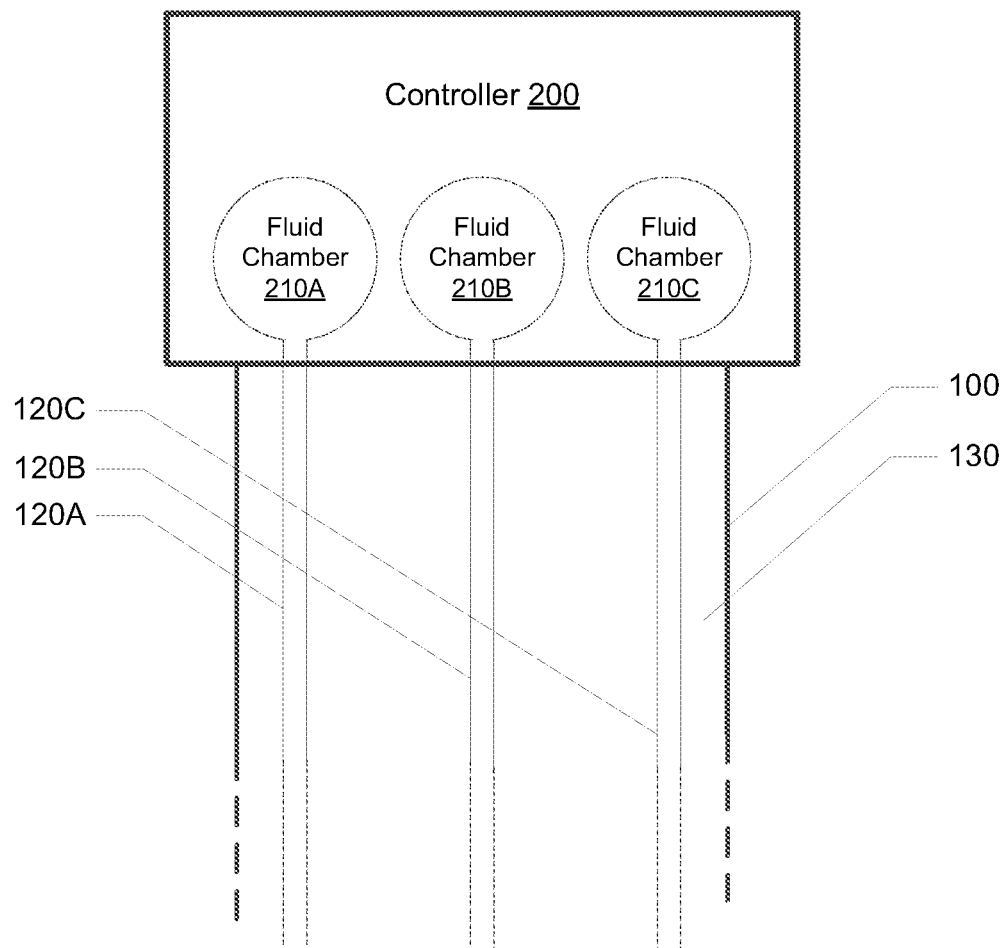
FIG. 2 depicts a controller for a hydraulically driven surgical apparatus, in accordance with some example embodiments.

FIG. 2 depicts a controller 200 for the hydraulically driven surgical apparatus 100, in accordance with some example embodiments. In some example embodiments, the surgical apparatus 100 may be coupled with the controller 200, which may be configured to steer the tube 110 of the surgical apparatus 100. For instance, as noted, the tube 110 may be steered, via hydraulic forces, into alignment with a treatment location such as, for example, the site of an aneurysm and/or the like.

Referring to FIG. 2, the controller 200 may include one or more fluid chambers including, for example, a first fluid chamber 210A, a second fluid chamber 210B, and a third fluid chamber 210C. Each fluid chamber may be filled with a liquid and may be coupled with a channel in the tube 110 of the surgical apparatus 100. For example, as shown in FIG. 2, the first fluid chamber 210A may be coupled with the first channel 120A, the second fluid chamber 210B may be coupled with the second channel 120B, and the third fluid chamber 210C may be coupled with the third channel 120C. In some example embodiments, the fluid pressure in a channel may be controlled via the corresponding fluid chamber. For instance, the fluid pressure in the first channel 120A may be increased by at least compressing the first fluid chamber 210A. The fluid pressure in the second channel 120B may be increased by at least compressing the second fluid chamber 210B. Alternatively and/or additionally, the fluid pressure in the third channel 120C may be increased by at least compressing the third fluid chamber 210C.

In some example embodiments, the controller 200 may be configured to receive one or more inputs. For example, a user may provide mechanical, digital, and/or haptic inputs indicative of a desired deformation in the tube 110. Alternatively and/or additionally, the user may provide inputs indicative of a desired change in the fluid pressure in the first channel 120A, the second channel 120B, and/or the third channel 120C. Meanwhile, the controller 200 may respond to these inputs by at least applying compression against the first fluid chamber 210A, the second fluid chamber 210B, and/or the third fluid chamber 210C. The controller 200 may apply sufficient compression to achieve the desired deformation in the tube 110. Alternatively and/or additionally, the controller 200 may apply sufficient compression to achieve the desired change in fluid pressure in the first channel 120A, the second channel 120B, and/or the third channel 120C.

As noted, changing the fluid pressure in the first channel 120A, the second channel 120B, and/or the third channel 120C may cause a deformation in one or more portions of the tube 110. For example, the controller 200 may respond to inputs from the user by at least compressing the third fluid chamber 210C. Compressing the third fluid chamber 210C may increase the fluid pressure in the third channel 120C, thereby causing the formation of a bend in the tube 110.

Figure 3A:
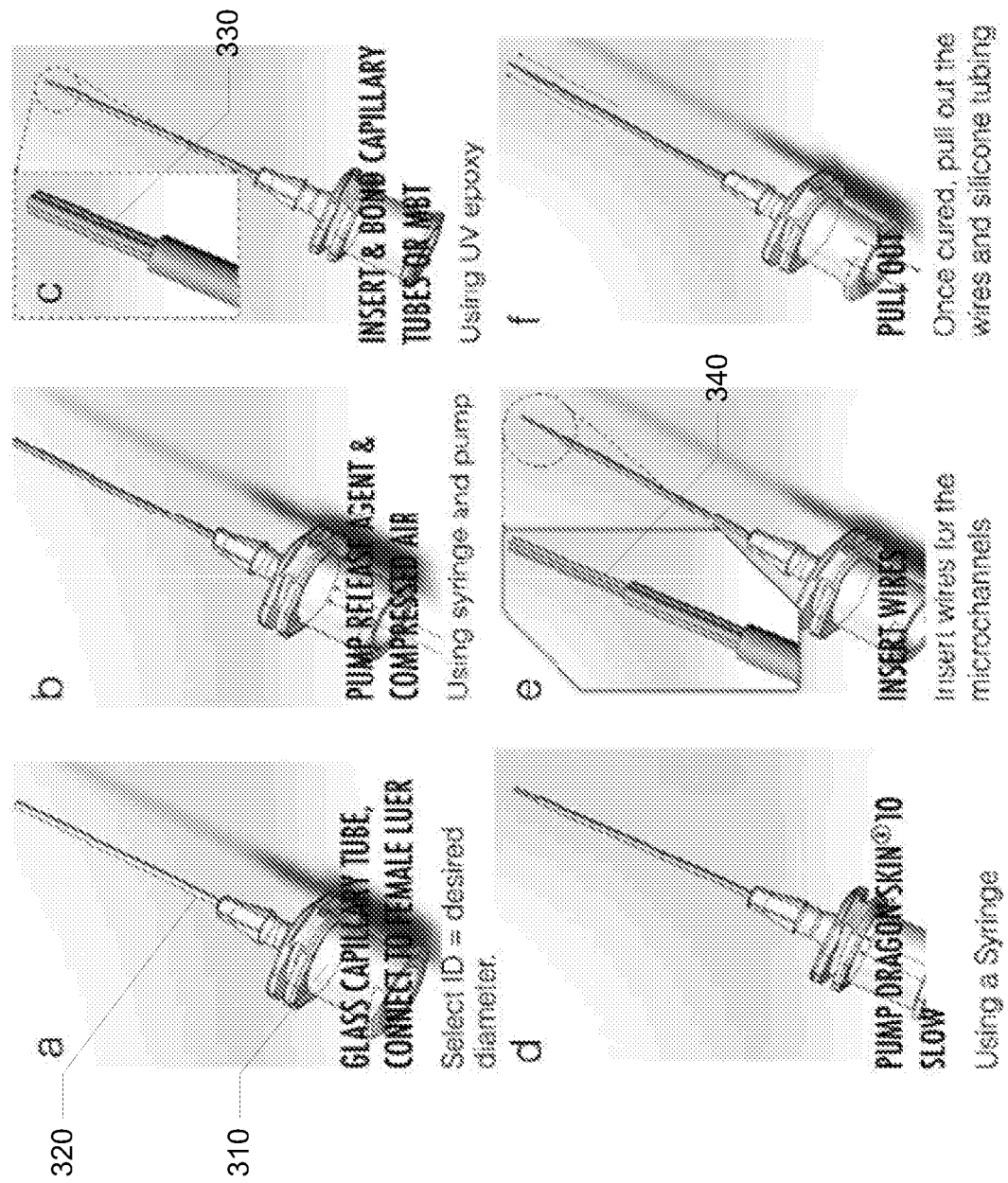
FIG. 3A depicts an extrusion technique for fabricating a hydraulically driven surgical apparatus, in accordance with some example embodiments.

In some example embodiments, tube 110 of the surgical apparatus 100, for example, as shown in FIGS. 1A-F, may be formed using a variety of different techniques including, for example, extrusion, molding, and/or the like. FIG. 3A depicts an extrusion technique for fabricating the tube 110, in accordance with some example embodiments.

Referring to FIG. 3A, an extrusion technique may be used to form the tube 110, which may include the tube 110 having, for example, the first channel 120A, the second channel 120B, the third channel 120C, and/or the fourth channel 130. In some example embodiments, the tube 110 may be formed using a tubing 310 having an inner diameter that is equivalent to a desired outer diameter of the tube 110. The tubing 310 may be any type of tubing including, for example, a glass capillary tube and/or the like. As shown in FIG. 3A, the tubing 310 may be attached to a connector 320, for example, using glue. The connector 320 may be a female Luer lock and/or any other type of connector. A release agent may be pumped through the tubing 310 using a syringe (not shown) and/or any other pumping mechanism coupled with the connector 320. To remove any excess release agent, a compressed liquid and/or gaseous substance (e.g., air and/or the like) may subsequently be pumped through the tubing 310, thereby leaving a thin layer of the release agent on the inner walls of the tubing 310.

As shown in FIG. 3A, additional tubes 330 may be positioned inside the tubing 310 and coated with the release agent. The additional tubes 330 may be any type of tubes including, for example, glass capillary tubes and/or the like. Furthermore, the additional tubes 330 may be a multi-bore tube and/or individual tubes. The additional tubes 330 may and/or may not be bonded to the tubing 310 using an epoxy such as, for example, an ultraviolet (UV) epoxy and/or the like.

In some example embodiments, the tubing 310 and the additional tubes 330 may be filled with a silicone rubber (e.g., a two part biocompatible platinum cure silicone rubber), which may be pumped into the tubing 310 and/or the additional tubes 330 using the syringe coupled with the connector 320. The silicone rubber may be mixed with a contrast agent such as, for example tantalum and/or the like, in order to enhance the visibility of the resulting surgical apparatus for medical imaging. One or more rods 340 may be slipped through each of the additional tubes 330. It should be appreciated that the additional tubes 330 may align the rods 340. The rods 340 may be formed from any material having sufficient rigidity including, for example, rhenium (Re), tungsten (W), and/or the like. Upon curing the silicon rubber, the rods 340 may be removed and the resulting tube 110 may be removed from the tubing 310.

Figure 3B:
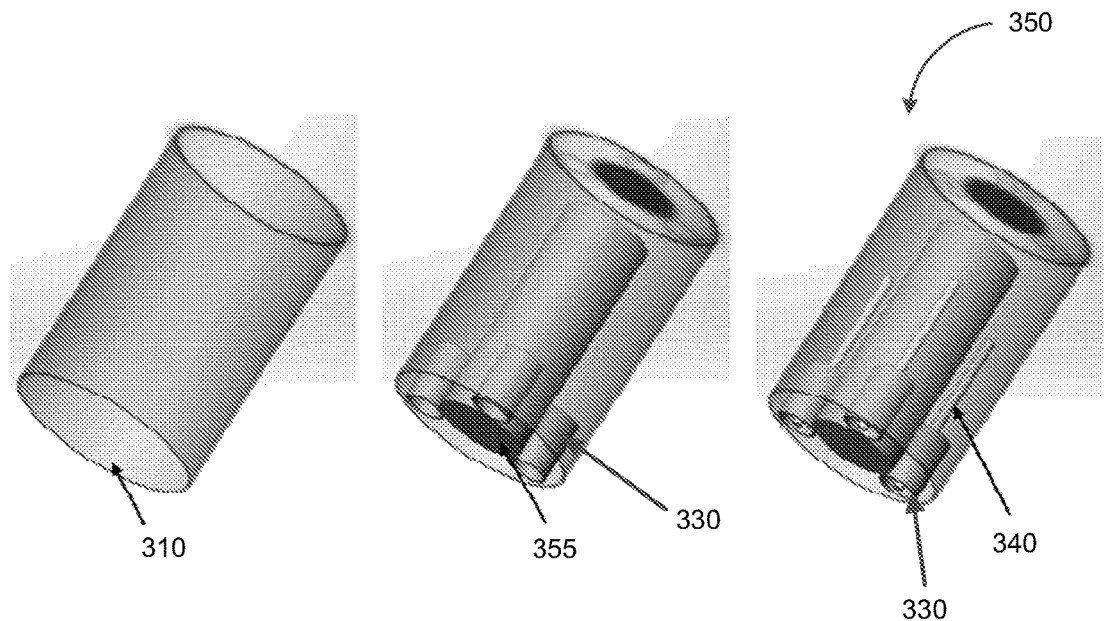
FIG. 3B depicts another assembly for fabricating a hydraulically driven surgical apparatus, in accordance with some example embodiments.

FIG. 3B depicts another assembly 350 for fabricating the tube 110, in accordance with some example embodiments. Referring to FIGS. 3A-B, a solid rod 355 may be inserted in the tubing 310 in order to create a lumen serving as a passageway for a substance and/or other apparatuses (e.g., guidewires, catheters, hollow tubes, fluid-filled tubes, and/or the like).

Figure 3C:
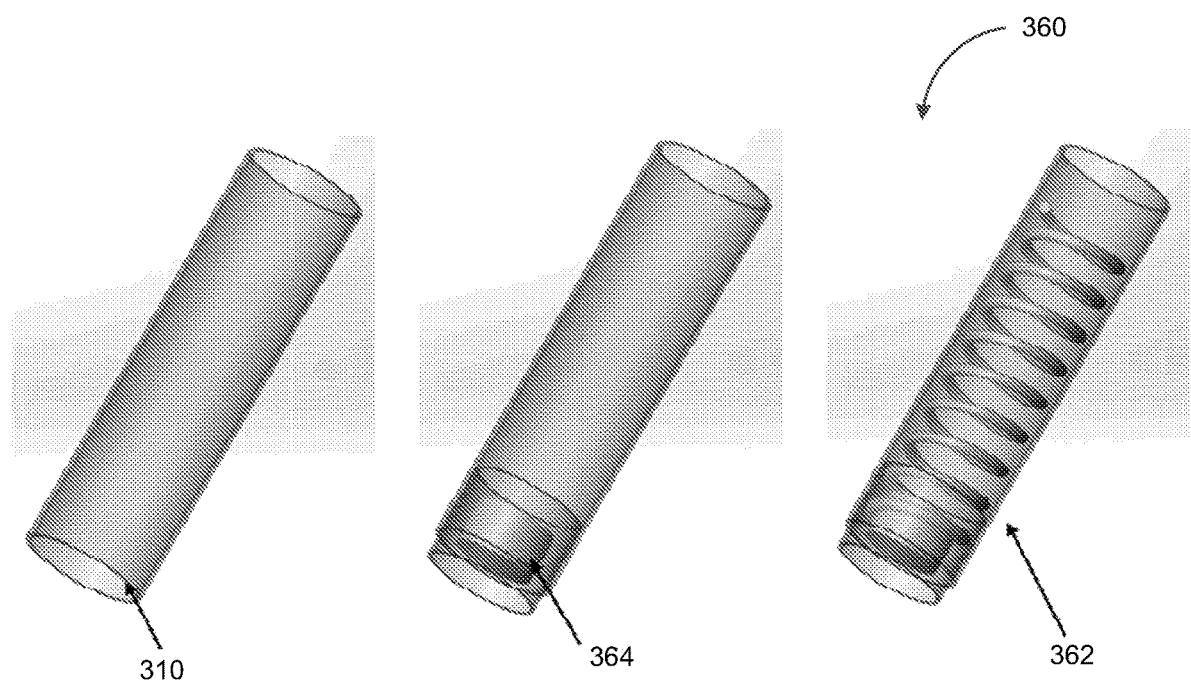
FIG. 3C depicts another assembly for fabricating a hydraulically driven surgical apparatus, in accordance with some example embodiments.

FIG. 3C depicts another assembly 360 for fabricating the tube 110, in accordance with some example embodiments. Referring to FIGS. 3A and 3C, a spring 352 may be inserted into the tubing 310 where the spring 362 may be aligned by an inner tube 364 positioned, for example, at a center of the spring 362. In some example embodiments, the assembly 360 may be used to form the tube 110 having the configuration shown in FIG. 1C, in which the helix fourth channel 130 traverses laterally through the interior of the tube 110.

Figure 4A:
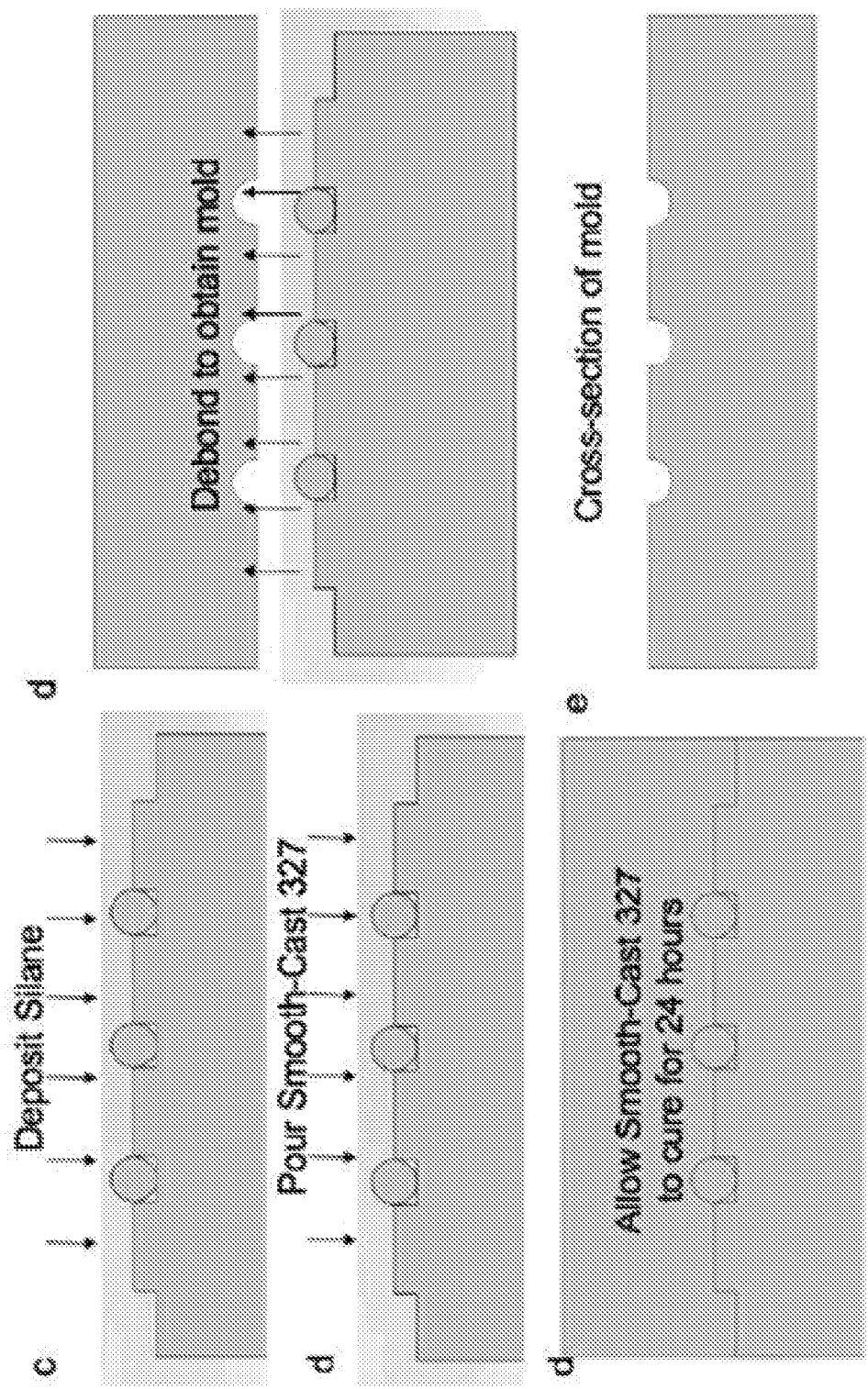
FIG. 4A depicts a molding technique for fabricating the hydraulically driven surgical apparatus, in accordance with some example embodiments.
Figure 4B:
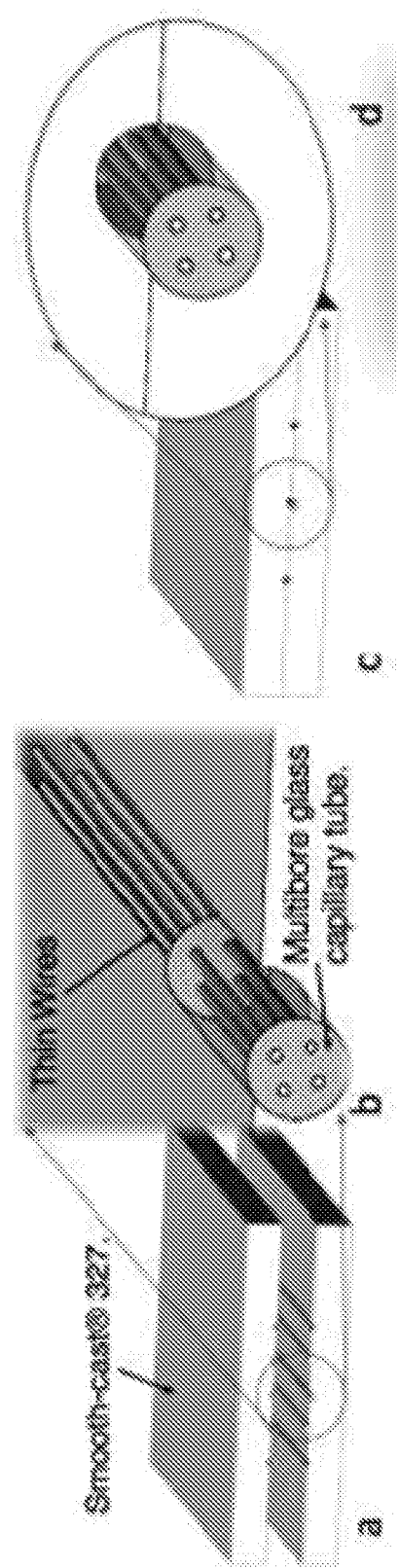
FIG. 4B depicts a molding technique for fabricating the hydraulically driven surgical apparatus, in accordance with some example embodiments.

FIGS. 4A-B depict a molding technique for fabricating the tube 110, in accordance with some example embodiments. Referring to FIG. 4A, a mold may be prepared by assembling, on a microscope slide, circular and/or rectangular tubes in parallel. The diameter D of the circular tubes may be equivalent to the desired diameter of the tube 110 while the height of the rectangular tubes may be $$\frac{D}{2}.$$

For example, if the desired diameter for the tube 110 is 500 μm, tubes that are 500 μm in diameter may be laid out in parallel on a microscope slide as shown in FIG. 4. Similarly, if the desired diameter for the tube 110 is 1 millimeter, tubes that are 1 millimeter in diameter may be placed in parallel on a microscope slide. In various example embodiments, the tubes may or may not be bonded to the microscope slide using an epoxy such as, for example, an ultraviolet (UV) epoxy and/or the like.

In some example embodiments, silane may be deposited onto the assembly including the tubings bonded to the microscope slide. The silane may be deposited via chemical vapor deposition (e.g., under a 0.05 megapascals (MPa) vacuum for one hour). The silane may provide a nanometer thick hydrophobic coating on the surface of the tubings.

Furthermore, the silane may provide flat glass strips, which may enable easy demolding. A molding material such as, for example, a two-part polyurethane plastic, may be poured onto the assembly and degassed. Upon curing, the molding material may be peeled off from the assembly of tubes to form rigid mold having a smooth surface.

As shown in FIG. 4B, multi-bore tubes may be placed in the mold and covered with a silicone rubber (e.g., a two part biocompatible platinum cure silicone rubber). Furthermore, the silicone rubber may be cured to form the tube 110 of the surgical apparatus 100. As noted, the multi-bore tubes may align one or more rods for creating the channels with the tube 110. The rods may be formed from any material exhibiting sufficient rigidity such as, for example, rhenium (Re), tungsten (W), and/or the like.

To further illustrate, as shown in FIG. 4B, a 4-bore tube may be used to fabricate the tube 110 having four channels. If a tubing with an outer diameter of 500 μM is used to fabricate a 500 μm tube 110, then the diameter of the individual bores may be 127 μm while the rods may have a diameter of 50 μm. Alternatively and/or additionally, if a tubing with an outer diameter of 1 millimeter is used to fabricate a 1 millimeter tube 110, then the diameter of the individual bores may be 127 μm while the rods may have a diameter of 100 μm.

Figure 5:
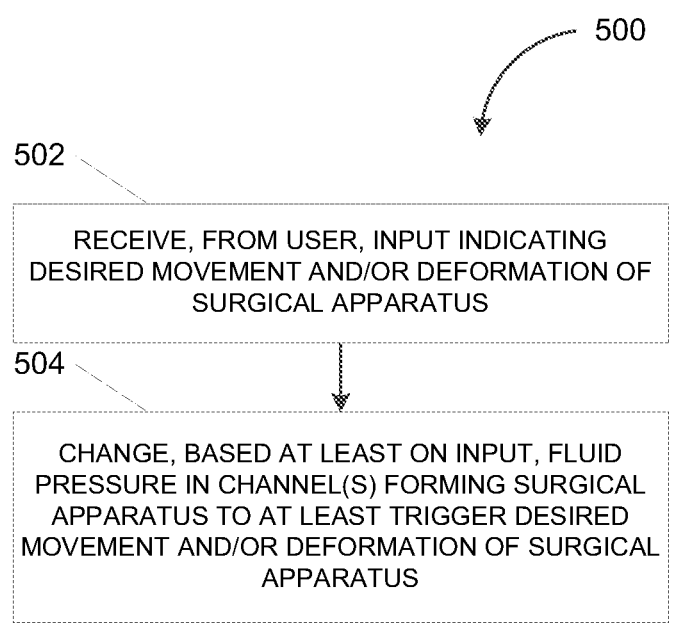
FIG. 5 depicts a flowchart illustrating a process for hydraulically driven endovascular neurosurgery, in accordance with some example embodiments.

FIG. 5 depicts a flowchart illustrating a process 500 for hydraulically driven endovascular neurosurgery, in accordance with some example embodiments. Referring to FIG. 5, the process 500 may be performed by the controller 200 in order to trigger a deformation of the tube 110.

At 502, the controller 200 may receive, from a user, an input indicating a desired deformation of the tube 110. For example, a user may provide a mechanical, digital, electrical, and/or haptic input indicative of a desired deformation in the tube 110. The surgical apparatus 100 may include the tube 110 having a plurality of channels including, for example, the first channel 120A, the second channel 120B, the third channel 120C, and/or the third channel 130. As noted, the tube 110 may be steered, for example, during endovascular neurosurgery, to align one or more portions of the tube 110 with a treatment location (e.g., site of aneurysm). Alternatively and/or additionally, the deformation of the tube 110 may actuate one or more surgical tools (e.g., gripper, cutter, drill, cauterizer, and/or the like) coupled with the tube 110.

At 504, the controller 200 may change, based on the input, a fluid pressure in one or more channels in the tube 110 to at least trigger the desired deformation of the tube 110. In some example embodiments, the fluid pressure in a channel may be changed via the fluid chamber coupled with the channel. For instance, as shown in FIG. 2, the fluid pressure in the first channel 120A may be increased by at least compressing the first fluid chamber 210A. The fluid pressure in the second channel 120B may be increased by at least compressing the second fluid chamber 210B. Alternatively and/or additionally, the fluid pressure in the third channel 120C may be increased by at least compressing the third fluid chamber 210C. As noted, changing the fluid pressure in a channel may trigger a deformation of the tube 110. For example, as shown in FIGS. 1A-B, increasing the fluid pressure in the third channel 120C and/or a different channel may trigger the formation of a bend in one or more portions of the tube 110. Alternatively and/or additionally, as shown in FIG. 1C, changing the fluid pressure in the helix fourth channel 130 may trigger a spiraling motion in the tube 110.

Figure 6:
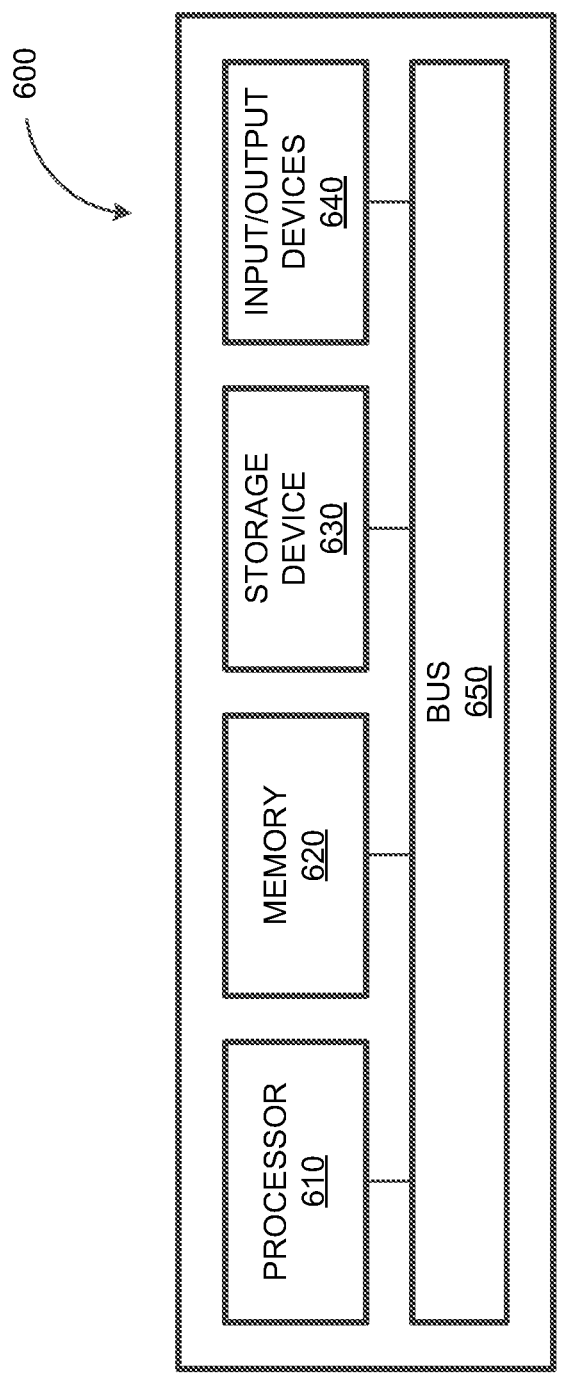
FIG. 6 depicts a block diagram illustrating a computing system, in accordance with some example embodiments.

FIG. 6 depicts a block diagram illustrating a computing system 600 consistent with implementations of the current subject matter. Referring to FIGS. 1-6, the computing system 600 can be used to implement the controller 200 and/or any components therein.

As shown in FIG. 5, the computing system 600 can include a processor 610, a memory 620, a storage device 630, and input/output devices 640. The processor 610, the memory 620, the storage device 630, and the input/output devices 640 can be interconnected via a system bus 650. The processor 610 is capable of processing instructions for execution within the computing system 600. Such executed instructions can implement one or more components of, for example, the controller 200. In some implementations of the current subject matter, the processor 610 can be a single-threaded processor. Alternately, the processor 610 can be a multi-threaded processor. The processor 610 is capable of processing instructions stored in the memory 620 and/or on the storage device 630 to display graphical information for a user interface provided via the input/output device 640.

The memory 620 is a computer readable medium such as volatile or non-volatile that stores information within the computing system 600. The memory 620 can store data structures representing configuration object databases, for example. The storage device 630 is capable of providing persistent storage for the computing system 600. The storage device 630 can be a floppy disk device, a hard disk device, an optical disk device, or a tape device, or other suitable persistent storage means. The input/output device 640 provides input/output operations for the computing system 600. In some implementations of the current subject matter, the input/output device 640 includes a keyboard and/or pointing device. In various implementations, the input/output device 640 includes a display unit for displaying graphical user interfaces.

According to some implementations of the current subject matter, the input/output device 640 can provide input/output operations for a network device. For example, the input/output device 640 can include Ethernet ports or other networking ports to communicate with one or more wired and/or wireless networks (e.g., a local area network (LAN), a wide area network (WAN), the Internet).

In some implementations of the current subject matter, the computing system 600 can be used to execute various interactive computer software applications that can be used for organization, analysis and/or storage of data in various (e.g., tabular) format (e.g., Microsoft Excel®, and/or any other type of software). Alternatively, the computing system 600 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 640. The user interface can be generated and presented to a user by the computing system 600 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus, comprising:
a tube enclosing a first channel filled with a first fluid; and
a controller including a first fluid chamber coupled with the first channel, wherein the controller is configured to at least
receive one or more haptic inputs indicating a desired deformation of the tube to perform an action associated with a surgical procedure,
determine a first fluid pressure in the first channel corresponding to the desired deformation of the tube, the determination based at least on a deflection angle of the tube associated with the desired deformation, a diameter of the tube, and a first radius of the first channel; and
perform the action associated with the surgical procedure by at least adjusting a compression against the first fluid chamber to achieve the first fluid pressure in the first channel.

2. The apparatus of claim 1, wherein the first channel comprises a channel traversing laterally through at least a portion of an interior of the tube, and wherein at least a portion of the tube bends in response to the change in the fluid pressure.

3. The apparatus of claim 1, wherein the first channel forms a helix, and wherein at least a portion of the tube twists in response to the change in the fluid pressure.

4. The apparatus of claim 1, wherein the tube further encloses a second channel filled with a second fluid, and wherein the controller further includes a second fluid chamber coupled with the second channel.

5. The apparatus of claim 4, wherein the controller is further configured to at least
determine, based at least on the deflection angle of tube associated with the desired deformation, the diameter of the tube, and a second radius of the second tube, a second fluid pressure in the second channel corresponding to the desired deformation, and,
perform the action associated with the surgical procedure by at least adjusting a compression against the second fluid chamber to achieve the second fluid pressure in the second channel.

6. The apparatus of claim 4, wherein the first channel has a different shape and/or dimension as the second channel.

7. The apparatus of claim 4, wherein the first channel traverses a different portion of the tube as the second channel.

8. The apparatus of claim 1, wherein the tube further encloses a third channel providing a passageway for a substance, a device, and/or a tool.

9. The apparatus of claim 1, wherein the first fluid includes a contrast agent for increasing a visibility of the tube to enable medical imaging.

10. The apparatus of claim 1, wherein the action comprises aligning the tube with a treatment location of the surgical procedure.

11. The apparatus of claim 1, wherein the action comprises advancing and/or retracting the tube.

12. The apparatus of claim 1, wherein the tube is coupled with a tool, and wherein the desired deformation of the tube actuates the tool to perform the action.

13. The apparatus of claim 1, wherein the controller is further configured to adjust the compression against the first fluid chamber in response to one or more mechanical inputs and/or digital inputs received from the user.

14. The apparatus of claim 1, wherein the tube is formed from a soft and/or deformable material.

15. The apparatus of any of claim 14, wherein the soft and/or deformable material includes a contrast agent for enhancing a visibility of the tube to enable medical imaging.

16. The apparatus of claim 1, wherein the first fluid pressure is further determined based on one or more of a bulk modulus of a material forming the first channel and a moment of inertia of the tube.

17. A method, comprising:
receiving one or more haptic inputs indicating a desired deformation of a tube to perform an action associated with a surgical procedure, the tube enclosing at least one channel filled with a fluid;

determining a fluid pressure in the at least one channel corresponding to the desired deformation of the tube, the determining based at least a deflection angle of the tube associated with the desired deformation, a diameter of the tube, and a radius of the at least one channel; and performing the action associated with the surgical procedure by at least adjusting a compression against a fluid chamber coupled with the at least one channel to achieve the fluid pressure in the at least one channel.

18. The method of claim 17, wherein the action comprises aligning the tube with a treatment location of the surgical procedure.

19. The method of claim 17, wherein the desired deformation of the tube performs the action by at least actuating a tool coupled with the tube.

20. The method of claim 17, wherein the fluid pressure is further determined based on one or more of a bulk modulus of a material forming the at least one channel and a moment of inertia of the tube.

* * * * *

UNITED STATES PATENT AND TRADEMARK OFFICE
CERTIFICATE OF CORRECTION

| | |
|---|---|
| PATENT NO. | : 11,266,811 B2 |
| APPLICATION NO. | : 16/334695 |
| DATED | : March 8, 2022 |
| INVENTOR(S) | : Friend et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 92 days.

Signed and Sealed this
Twenty-ninth Day of November, 2022

Katherine Kelly Vidal
*Director of the United States Patent and Trademark Office*